(12) United States Patent
Escher et al.

(10) Patent No.: US 10,993,464 B2
(45) Date of Patent: May 4, 2021

(54) THIOLS AS FLAVORING INGREDIENT

(71) Applicant: FIRMENICH SA, Satigny (CH)

(72) Inventors: Sina Dorothea Escher, Confignon (CH); Yvan Niclass, Perly (CH); Lionel Saudan, Geneva (CH)

(73) Assignee: Firmenich SA, Satigny (CH)

( * ) Notice: Subject to any disclaimer, the term of this patent is extended or adjusted under 35 U.S.C. 154(b) by 237 days.

(21) Appl. No.: 15/805,872

(22) Filed: Nov. 7, 2017

(65) Prior Publication Data

US 2018/0055077 A1  Mar. 1, 2018

Related U.S. Application Data

(63) Continuation-in-part of application No. 13/940,054, filed on Jul. 11, 2013, now abandoned, which is a continuation of application No. 12/826,047, filed on Jun. 29, 2010, now abandoned, which is a continuation of application No. 11/865,418, filed on Oct. 1, 2007, now abandoned, which is a continuation of application No. PCT/IB2006/051419, filed on May 5, 2006.

(30) Foreign Application Priority Data

May 13, 2005 (WO) .................. PCT/IB2005/001449

(51) Int. Cl.
  *C11B 9/00* (2006.01)
  *A23L 27/20* (2016.01)
  *C07C 323/12* (2006.01)
  *A23L 2/56* (2006.01)

(52) U.S. Cl.
  CPC ............. *A23L 27/20* (2016.08); *A23L 2/56* (2013.01); *A23L 27/2022* (2016.08); *A23L 27/2024* (2016.08); *C07C 323/12* (2013.01); *C11B 9/0011* (2013.01)

(58) Field of Classification Search
  CPC .. A23L 27/20; A23L 27/2022; A23L 27/2024; C11B 9/0011
  See application file for complete search history.

(56) References Cited

U.S. PATENT DOCUMENTS

| 4,120,845 | A  | 10/1978 | Kugele |
| 5,008,432 | A  | 4/1991  | Roberts |
| 2001/0031720 | A1 | 10/2001 | Gassenmeier et al. |
| 2003/0064146 | A1 | 4/2003  | Yusuf et al. |
| 2004/0037787 | A1 | 2/2004  | Dewis et al. |

FOREIGN PATENT DOCUMENTS

| EP | 1 249 446 B1 | 10/2002 |
| GB | 1 336 037    | 11/1973 |

OTHER PUBLICATIONS

Bauer et al., "Common Fragrance and Flavor Materials (Fourth Edition)," published online Nov. 5, 2001, Wiley-VCH Verlag GmbH, pp. 28, 186, 211, 212.
Campbell, "Lager," Encyclopedia of Food Microbiology, vol. 1-3, Elsevier. Online version available at http://knovel.com/web/portal/browse/display?_EXT_KNOVEL_DISPLAY_bookid=1870&VerticalID=0, pp. 1172-1176 (1999).
Collin et al., XP002398286, "Combinatorial Synthesis and Sensorial Properties of 21 Mercapto Esters," J. Agric. Food Chem, 51:3618-3622 (2003).
Engel et al., "Identification of New Sulfur-Containing Volatiles in Yellow Passion Fruits (*Passiflora edulis* f. flavicarpa)," J. Agric. Food Chem., 38:2249-2251 (1991).
Nobel, "Taste-Aroma Interactions," Trends in Food Science and Technology, 7:439-444, Dec. 1996.
Rossell, "Frying—Improving Quality," Woodhead Publishing, p. 320 (2001).
Vermeulen et al., "Polyfunctional thiols and drinkability of beer," Proceedings of the Congres—European Brewery Convention, 91/1-91/11 (2003).
International Search Report and Written Opinion, Appl. No. PCT/IB2006/051419, dated Sep. 25, 2006.
U.S. Appl. No. 11/865,418, Non-Final Rejection, dated May 1, 2009.
U.S. Appl. No. 11/865,418, Non-Final Rejection, dated Dec. 30, 2009.
U.S. Appl. No. 12/826,047, Non-Final Rejection, dated Jan. 3, 2012.
U.S. Appl. No. 12/826,047, Non-Final Rejection, dated May 2, 2012.
U.S. Appl. No. 12/826,047, Final Rejection, dated Nov. 15, 2012.
U.S. Appl. No. 13/940,054, Non-Final Rejection, dated Dec. 30, 2015.
U.S. Appl. No. 13/940,054, Final Rejection, dated Jan. 10, 2017.
U.S. Appl. No. 13/940,054, Advisory Action, dated Aug. 7, 2017.
U.S. Appl. No. 13/940,054, Advisory Action, dated Aug. 30, 2017.

*Primary Examiner* — Felicia C Turner

(74) *Attorney, Agent, or Firm* — Armstrong Teasdale LLP

(57) ABSTRACT

A method to confer, enhance, improve or modify the flavor properties of a flavoring composition or flavored article by adding to the composition or article the compound 3-mercaptoheptyl acetate or an optically active enantiomer thereof in an amount effective to provide a flavor base having top notes of the citrus-grapefruit, teas and/or peach type and/or red fruit. The compound is typically added to provide an amount of from 0.0001 to 500 ppm in the flavoring composition or flavored article. Also, the resultant flavored composition or flavored article.

20 Claims, No Drawings

THIOLS AS FLAVORING INGREDIENT

CROSS-REFERENCE TO RELATED APPLICATIONS

This application is a continuation-in-part of U.S. application Ser. No. 13/940,054 filed on Jul. 11, 2013, abandoned, which is a continuation of U.S. application Ser. No. 12/826,047 filed on Jun. 29, 2010, abandoned, which is a continuation of U.S. application Ser. No. 11/865,418 filed on Oct. 1, 2007, abandoned, which is a continuation of International application PCT/IB2006/051419 filed on May 5, 2006, expired, with the entire content of each of these applications being expressly incorporated herein by reference thereto.

TECHNICAL FIELD

The present invention relates to the field of flavor. More particularly, it concerns the use of a 3-mercaptoheptyl carboxylate and preferably 3-mercaptoheptyl acetate as a flavoring ingredient.

BACKGROUND

To the best of our knowledge, amongst the invention's compounds, only 3 mercaptoheptyl acetate has been reported in the literature (see S. Collin et al. in *J. Agr. Food Chem*, 2003, 3618) and only in the form of a crude reaction mixture. This acetate is described as having odor notes of the "onion, exotic fruit, candy" type. However, this prior art document does not report or suggest any flavor properties of the compounds of formula (I), or any use of said compound in the field of flavor.

SUMMARY OF THE INVENTION

The present invention now relates to the use of 3-mercaptoheptyl carboxylate in the form of any one of its stereoisomers or in the form of a mixture thereof. The invention's compounds are valuable favoring ingredients capable of imparting fruity, citrus and/or teas aftertaste with a well-balanced long-lastingness. The present invention concerns also the compositions or articles containing said compound.

In particular, the present invention relates to a method to confer, enhance, improve or modify the flavor properties of a flavoring composition or flavored article by adding to the composition or article the compound 3-mercaptoheptyl acetate or an optically active enantiomer thereof in an amount effective to provide a flavor base having top notes of the citrus-grapefruit, teas and/or peach type and/or red fruit.

The invention also relates to a flavoring composition that contains, as a flavoring ingredient, the compound 3-mercaptoheptyl acetate or an optically active enantiomer thereof in an amount effective to provide a flavor base having top notes of the citrus-grapefruit, teas and/or peach type and/or red fruit; at least one ingredient selected from the group consisting of a flavor carrier and a flavor base; and optionally at least one flavor adjuvant.

The invention also relates to a flavored article that contains, as a flavoring ingredient, the compound 3-mercaptoheptyl acetate or an optically active enantiomer thereof in an amount effective to provide a flavor base having top notes of the citrus-grapefruit, teas and/or peach type and/or red fruit; and a foodstuff base, typically a bakery, a dairy, a confectionary, a savory, an infusion, a soft drink, a flavored water or a juice product.

DETAILED DESCRIPTION OF THE PREFERRED EMBODIMENTS

As mentioned above, the invention concerns the use as flavoring ingredient of 3-mercaptoheptyl carboxylate, of formula

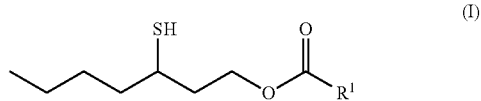

in an optically active or non-optically active form, wherein $R^1$ represents a $C_1$-$C_3$ alkyl group.

According to a particular embodiment of the invention, the acetate derivatives, $R^1$ representing a methyl group, are particularly appreciated for their flavors. Additionally, 3-mercaptoheptyl acetate is a particularly preferred flavoring compound.

The invention's compounds are valuable flavoring ingredients capable of imparting fruity, citrus and/or teas bottom notes, which results in a very good and appreciated aftertaste or long-lastingness of the flavor.

In general a flavor is characterized by its top notes as well as the bottom notes, the former defining the first impression in the mouth and the latter determining the impression in the month and the length of the organoleptic effect. Flavoring ingredients capable of imparting well-balanced bottom notes are relatively rare and for that reasons highly desirable for the flavorists.

In particular, by means of non-limiting examples of the invention, one may cite 3-mercaptoheptyl acetate which possesses a relatively weak top note reminding of a peach, citrus and tea tonality. This top note is followed by highly appreciated and performing bottom notes of the green/black tea type as well as of the citrus-grapefruit and fruity-pear-peach type which render said compound a very useful flavoring ingredient.

The two enantiomers of the cited acetate, namely the (R) and the (S) ones, are also valuable flavoring ingredients, which can be used in a similar way. Amongst said enantiomers the most appreciated is the (S) one, which has a taste very close to the one of the racemate, although its grapefruit type note is weaker than the one of the racemate.

The invention's compounds are derivatives of 1-methoxy-3-heptanethiol, described in EP 1249446, and are structurally close to 3-mercaptohexyl acetate or butanoate, described by K.-H. Engel in *J. Agr. Food Chem*, 1991, 2249.

However, despite the structural resemblance between compounds (I) and those of the prior art, the former have flavor properties quite unexpected and distinct. 1-Methoxy-3-heptanethiol is described as having tropical fruit and, in particular, berries flavor notes, while 3-mercaptohexyl acetate is described as having an extremely fruity flavor, suggestive of passion fruit with a Riesling type note.

In particular, 3-mercaptoheptyl acetate distinguishes itself from the cited prior art compounds by having an original flavor profile and especially aftertaste. As will be shown hereinbelow by the examples, 3-mercaptoheptyl acetate distinguishes itself from 1-methoxy-3-heptanethiol by not having a tropical fruit character as well as by its much weaker top notes and its much more pronounced aftertaste, as well as by the presence of teas and pear-peach notes which are absent from the prior art compound.

Furthermore, 3-mercaptoheptyl acetate distinguishes itself from 3-mercaptohexyl acetate by its overall flavor profile and in particular by not having the typical sulfury, guava-passion fruit note of the prior art compound.

The 3-mercaptoheptyl acetate in added either in its racemic form or in an optically active form (i.e., S- or R-enantiomer) to provide a totally unexpected flavor tonality compared to other 3-mercaptalkyl acetates. As noted herein, 3-mercaptoheptyl acetate provides citrus-grapefruit, teas and/or peach type and/or red fruit tonality to articles to which it is added in the appropriate amounts.

The 3-mercaptoheptyl acetate compound provides unexpectedly surprising flavor tonalities, which are quite different from what could be expected based on the odor properties of that compound and similar compounds. As per the above-mentioned S. Collin et al. article, the following odor notes were observed for various 3-mercaptoalkyl acetate compounds:

| Compound | Odor Tonality |
| --- | --- |
| 3-mercaptopropyl acetate | Grilled, roasted meat |
| 3-mercaptobutyl acetate | Pungent, stinging, nettle, hazelnut |
| 3-mercaptopentyl acetate | Exotic fruit, candy |
| 3-mercaptohexyl acetate | Candy, blackcurrant, passion fruit |
| 3-mercaptoheptyl acetate | Onion, exotic fruit, candy |
| 3-mercaptooctyl acetate | Citrus fruit peel, *rhubarb*, carrot |
| 3-mercaptononyl acetate | Carrot, sweet |

The 3-mercaptoheptyl acetate compound provides in foodstuffs to which it is added or in which it is present, a very different flavor tonality from the odor characters described in the previous table. It is of particular interest to flavorists that the 3-mercaptoheptyl acetate when added to foodstuffs can provide a flavor note of citrus-grapefruit, teas and/or peach type and/or red fruit without flavors of onion, grilled meat, rhubarb or carrot which would be expected from that compound as well as from the other 3-mercaptoalkyl acetate compounds.

In the methods and flavored articles of the invention, the 3-mercaptoheptyl acetate compound is typically added or present in an amount of from 0.0001 to 500 ppm, and preferably between 0.0001 and 120 ppm, in the flavoring composition or flavored article. Preferably, the compound is added or present in an amount of from 0.0003 to 5 ppm in the flavored article.

The 3-mercaptoheptyl acetate compound can be added directly to the flavoring composition or flavored article. The flavoring composition can be added to the flavored article. The flavoring composition typically comprises at least one ingredient selected from the group consisting of a flavor carrier and a flavor base; and optionally at least one flavor adjuvant. In this composition, the compound is present in an amount of from 0.0000001 to 0.03% by weight thereof and preferably from 0.0000002 to 0.01% by weight thereof.

In particular, the 3-mercaptoheptyl acetate compound is desirable because it possesses and imparts a relatively weak top note reminding of a peach, citrus and tea tonality. This top note is followed by highly appreciated and performing bottom notes of the green/black tea type as well as of the citrus-grapefruit and fruity-pear-peach type which render the compound a very useful flavoring ingredient. These top and bottom notes are further described in the following examples.

Another object of the present invention is a compound of formula (I), as defined above, in an optically active form. Indeed said enantiomer-enriched form is new as the prior art cited above mentions only a racemate.

As mentioned above, the invention concerns the use as perfuming ingredients of the compounds of formula (I). In other words, it concerns a method to confer, enhance, improve or modify the flavor properties, and in particular its long-lastingness, of a flavoring composition or of a flavored article, which method comprises adding to said composition or article an effective amount of at least a compound of formula (I).

By "use of a compound of formula (I)" it has to be understood here also the use of any composition containing compound (I) and which can be advantageously employed in the flavors industry as active ingredients.

Said compositions, which in fact can be advantageously employed as flavoring ingredient, are also an object of the present invention.

Therefore, another object of the present invention is a flavoring composition comprising:
i) as flavoring ingredient, at least one invention's compound as defined above;
ii) at least one ingredient selected from the group consisting of a flavor carrier and a flavor base; and
iii) optionally at least one flavor adjuvant.

By "flavor carrier" we mean here a material which is practically neutral from a flavor point of view, i.e., that does not significantly alter the organoleptic properties of flavoring ingredients. Said carrier may be a liquid or a solid.

As liquid carrier one may cite, as non-limiting examples, an emulsifying system, i.e. a solvent and a surfactant system, or a solvent commonly used in flavors. A detailed description of the nature and type of solvents commonly used in flavor cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. As non-limiting examples of solvents commonly used in flavors, one can cite compounds such as water, propylene glycol, triacetine, triethyl citrate, benzylic alcohol, ethanol, vegetal oils or terpenes.

As solid carrier one may cite, as non-limiting examples, absorbing gums or polymers, or yet encapsulating materials. Examples of such materials, for example, may comprise wall-forming and plasticizing materials, such as mono-, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "flavor base" we mean here a composition comprising at least one flavoring co-ingredient.

Said flavoring co-ingredient is not of the formula (I). Moreover, by "flavoring co-ingredient" it is meant here a compound, which is used in flavoring preparation or composition to impart a hedonic effect. In other words such a co-ingredient, to be considered as being a flavoring one, must be recognized by a person skilled in the art as being able to impart or modify in a positive or pleasant way the taste of a composition, and not just as having a taste.

The nature and type of the flavoring co-ingredients present in the base do not warrant a more detailed description here, which in any case would not be exhaustive, the skilled person being able to select them on the basis of its general knowledge and according to intended use or application and the desired organoleptic effect. In general terms, these flavoring co-ingredients belong to chemical classes as varied as alcohols, aldehydes, ketones, esters, ethers, acetates, nitriles, terpene hydrocarbons, nitrogenous or sulphurous heterocyclic compounds and essential oils, and said flavoring co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of flavor. It is also understood that said co-ingredients may also be compounds known to release in a controlled manner various types of flavoring compounds.

According to a particular embodiment of the invention's, particularly appreciated flavor bases are those capable of imparting top notes of the citrus-grapefruit, teas and/or peach type and/or red fruit (e.g. berries or tropical). Indeed, with such flavor bases, the compounds of formula (I) are capable of providing a highly appreciated long-lastingness of the flavor.

Generally speaking, by "flavor adjuvant" we mean here an ingredient capable of imparting additional added benefit such as a color, a particular light resistance, chemical stability, etc. A detailed description of the nature and type of adjuvant commonly used in flavoring bases cannot be exhaustive, but it has to be mentioned that said ingredients are well known to a person skilled in the art.

An invention's composition consisting of at least one compound of formula (I) and at least one flavor carrier represents a particular embodiment of the invention as well as a flavoring composition comprising at least one compound of formula (I), at least one flavor carrier, at least one flavor base, and optionally at least one flavor adjuvant.

It is useful to mention here that the possibility to have, in the compositions mentioned above, more than one compound of formula (I) is important as it enables the flavorist to prepare accords, flavors, possessing the flavor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a flavoring composition according to the invention.

Moreover, a compound of formula (I) can be advantageously incorporated into flavored articles to positively impart, or modify, the taste of said articles. Consequently, a flavored article comprising:
i) as flavoring ingredient, at least one compound of formula (I), as defined above, or an invention's flavoring composition; and
ii) a foodstuff base,
is also an object of the present invention.

For the sake of clarity, it has to be mentioned that, by "foodstuff base", we mean here an edible product, e.g. a food or a beverage. Therefore, a flavored article according to the invention comprises the functional formulation, as well as optionally additional benefit agents, corresponding to a desired edible product, e.g. a foods or beverages, and a flavor effective amount of at least an invention's compound.

The nature and type of the constituents of the foodstuffs or beverages do not warrant a more detailed description here, which in any case would not be exhaustive, the skilled person being able to select them on the basis of its general knowledge and according to the nature of said product.

Non-limiting examples of suitable foodstuff bases include a bakery, a dairy, a confectionary, a savory, an infusion, a soft drink, a flavored water and a juice product. In particular one may cite foodstuff bases such as a chewing gum, a yogurt, milk, a hot or cold tea drink, a carbonated or non-carbonated soft drinks, potato chips, a soup, a fruit juice.

The proportions in which the compounds according to the invention can be incorporated into the various aforementioned articles or compositions vary within a wide range of values. These values are dependent on the nature of the article to be flavored and on the desired organoleptic effect as well as the nature of the co-ingredients in a given base when the compounds according to the invention are mixed with flavoring co-ingredients, solvents or additives commonly used in the art.

In the case of flavoring compositions, the concentration of these flavoring compounds can be varied determined during routine testing or optimization. Typical concentrations are in the order of 0.5% to 5% by weight, or even more, of the compounds of the invention based on the weight of the consumer product into which they are incorporated. Concentrations lower than these, such as in the order of 0.01% to 0.5% by weight, can be used when these compounds are incorporated into flavored articles, percentage being relative to the weight of the article. The 3-mercaptoheptyl acetate compound or enantiomer thereof is typically added or present in an amount of from 0.0001 to 12 ppm in the flavoring composition or flavored article. Thus, a wide range of concentrations or amounts can be used depending upon the flavoring effect to be achieved.

EXAMPLES

The following examples are further illustrative of the present invention embodiments, and further demonstrate the advantages of the invention's compounds relative to prior art teachings. The abbreviations contained in these examples have the usual meaning in the art, the temperatures are indicated in degrees centigrade (° C.); the NMR spectral data were recorded in $CDCl_3$ (if not stated otherwise) with a 400 MHz machine for $^1H$ and $^{13}C$, the chemical displacements δ are indicated in ppm with respect to TMS as standard and the coupling constants J are expressed in Hz.

Example 1

Synthesis of 3-mercaptoheptyl acetate

A) 3-Hydroxyheptyl acetate: To an ice-cooled and stirred solution of heptane-1,3-diol (6.60 g, 50 mmol) in pyridine (50 ml) was added dropwise acetic acid chloride (3.92 g, 50 mmol). The stirring was continued at room temperature for 16. Workup with diethyl ether and flash chromatography (cyclohexane-ethyl acetate 75:25) gave 6.00 g of the desired acetate (69%).
$^1$H-NMR (after exchange with $D_2O$): 4.33 (ddd, J=11.3, 8.7, 8.2, 1H); 4.16 (dt, J=11.3, 5.6, 1H); 3.66 (m, 1H); 2.06 (s, 3H); 1.82, 1.67, 1.43, 1.32 (4 m, 8H); 0.91 (t, J=7.1, 3H).

$^{13}$C-NMR: 171.49 (s); 68.68 (d); 61.88 (t); 37.24 (t); 36.32 (t); 27.81 (t); 22.71 (t); 21.01 (q); 14.06 (q).

B) 3-(Acetylthio)heptyl acetate: To a solution of 1,3-dimethyl-2-fluoropyridinium 4-methylbenzenesulfonate (4.90 g, 16.5 mmol) in acetone-benzene 1:1 (v/v, 40 ml), triethylamine (2.3 ml, 16.5 mmol) was added, followed by the acetate obtained under A) (2.61 g, 15 mmol). The clear solution was stirred for 1 h. Thioacetic acid (1.17 ml, 16.5 mmol) and triethylamine (2.3 ml, 16.5 mmol) in acetone-benzene 1:1 (5 ml) were added. The mixture was heated at 80° (bath temperature) for 3 hour. The solvents were then partly removed at in vacuo. Workup (diethyl ether) followed by purification of the crude product (3.73 g) by flash chromatography with cyclohexane-ethyl acetate 9:1 afforded 1.44 g (41%) of desired product in 94% purity.

$^{1}$H-NMR: 4.13 (t, J=6.5, 2H); 3.61 (m, 1H); 2.32 (s, 3H); 2.06 (s, 3H); 1.99, 1.84, 1.61, 1.33 (4 m, 8H); 0.89 (t, J=7.2, 3H).

$^{13}$C-NMR: 195.49 (s); 171.07 (s); 61.98 (t); 41.24 (d); 34.65 (t); 33.64 (t); 30.76 (q); 28.88 (t); 22.47 (t); 20.97 (q); 13.96 (q).

C) 3-Mercaptoheptanol: To an ice-cooled and stirred suspension of LiAlH$_4$ (285 mg, 7.5 mmol) in diethyl ether (40 ml) was added dropwise a solution of thioacetate obtained under B) (1.16 g, 5 mmol) in diethyl ether (30 ml). Workup with diethyl ether gave 770 mg of crude mercaptoalcohol that was purified by flash chromatography (pentane-diethyl ether 7:3) and the desired compound was obtained as colorless oil (680 mg, 92%).

$^{1}$H-NMR (after exchange with D$_2$O): 3.83 (m, 2H); 2.94 (m, 1H); 1.98, 1.67 1.51 1.33 (4 m, 8H); 1.41 (d, J=7.7, 1H), 0.91 (t, J=7.6, 3H).

$^{13}$C-NMR: 60.76 (t); 41.32 (t); 39.29 (t); 38.03 (d); 29.18 (t); 22.42 (t); 14.02 (q).

D) 3-Mercaptoheptyl acetate: To a stirred solution of the alcohol obtained under C) (444 mg, 3 mmol) in dichloromethane (2 ml) was added dropwise a solution of acetic acid chloride (236 mg, 3 mmol) in dichloromethane (1 ml). After 3 hours, the reaction mixture was concentrated to ca. 1 ml in a Vigreux apparatus, and the concentrate was purified by flash chromatography with pentane-diethyl ether 95:5 as eluant. The desired compound was obtained as colorless oil (400 mg, 70%).

$^{1}$H-NMR: 4.24 (m, 2H); 2.87 (m, 1H); 2.05 (s, 3H); 2.02, 1.73, 1.69, 1.49, 1.33 (5 m, 8H); 1.40 (d, J=7.6, 1H), 0.92 (t, J=7.1, 3H).

$^{13}$C-NMR: 171.00 (q), 62.27 (t); 38.83 (t); 37.75 (t); 37.62 (d); 29.13 (t); 22.41 (t); 20.97 (q); 14.00 (q).

Example 2

Synthesis of the Enantiomers of 3-mercaptoheptyl acetate (R)-1,3-Heptanediol was obtained according to the procedure described in EP 1249446.

(S)-Methyl 3-hydroxyheptanoate was obtained according to W. Oppolzed et al. in Tetrahedron Letters, 1992, pg. 2439.

A) Preparation of (S)-3-Mercaptoheptyl Acetate i) (R)-3-hydroxyheptyl acetate

To a solution at 0° C. of (R)-1,3-heptanediol (9.703 g, 73 mmol) in pyridine (74 ml) was added dropwise over a period of 45 minutes neat acetyl chlorid (5.3 ml, 74 mmol). The reaction is slightly exothermic and a heavy white precipitate formed immediately. At the end of the addition, the white slurry was further stirred at room temperature for 100 minutes. Then the reaction mixture was poured into a mixture of ice and H$_2$SO$_4$ 2N and extracted several times with Et$_2$O. The organic layers were combined, washed successively with H$_2$SO$_4$ 2N, H$_2$O, aqueous saturated NaHCO$_3$, brine and dried over anhydrous Na$_2$SO$_4$. After filtration, the solvent was removed under vacuum to give the crude compound. Purification by flash chromatography on silica gel eluted with a mixture of heptane/AcOEt (8/2) to give the desired product (9.404 g, 68%) as a pale yellow liquid.

Optical rotation: $\alpha_D$=−7.0 (c=5.0, CHCl$_3$, 20° C.).

$^{1}$H-NMR: 4.33 (ddd, J=11.3, 5.6, 5.1, 1H), 4.15 (dt, J=11.3, 5.6, 1H), 3.67 (br m, 1H), 2.17 (br d, J=0.6, 1H), 2.06 (s, 3H), 1.87-1.77 (m, 1H), 1.72-1.62 (m, 1H), 1.52-1.24 (m, 6H), 0.91 (t, J=7.3, 3H).

$^{13}$C-NMR: 171.5 (s), 68.7 (d), 61.9 (t), 37.2 (t), 36.3 (t), 27.8 (t), 22.7 (t), 21.0 (q), 14.1 (q).

ii) (R)-3-[(Methylsulfonyl)oxy]heptyl acetate

To a solution at 0° C. of (R)-3-hydroxyheptyl acetate (9.211 g, 49 mmol) in Et$_2$O (170 ml) was added Et$_3$N (20 ml, 142 mmol, 3 eq), followed by methanesulfonyl chloride (5.7 ml, 73 mmol, 1.5 eq). The cooling bath was removed and the reaction mixture was stirred at room temperature. After 90 minutes, the reaction mixture was poured into ice/water mixture and extracted several times with Et$_2$O. The organic layers were combined and washed with aqueous HCl 0.5 M, H$_2$O and dried over anhydrous Na$_2$SO$_4$. After filtration, the solvent was removed under vacuum to give crude (R)-3-[(methylsulfonyl)oxy]heptyl acetate (12.615 g, 49 mmol) as a yellow oil which was directly taken into the next step.

$^{1}$H-NMR: 4.83 (quint, J=6.1, 1H), 4.19 (t, J=6.4, 2H), 3.02 (s, 3H), 2.06 (s, 3H), 2.05-1.98 (m, 2H), 1.8-1.7 (m, 2H), 1.45-1.3 (m, 4H), 0.92 (t, J=6.9, 3H).

$^{13}$C-NMR: 170.9 (s), 80.2 (d), 60.2 (t), 38.6 (q), 34.5 (t), 33.4 (t), 26.9 (t), 22.4 (t), 20.9 (q), 13.9 (q).

iii) (S)-3-(Acetylthio)heptyl acetate

A 100 ml, four necked flask equipped with a mechanical stirring bar, a thermometer probe and an argon inlet/outlet was charged with cesium carbonate (9.58 g, 27 mmol, 1.1 eq) and NMP (45 ml). To this stirred pink suspension was added dropwise over 5 minutes thioacetic acid (4.9 ml, 69 mmol, 1.4 eq). The reaction mixture was further stirred at room temperature for 100 minutes. To this solution was added neat (R)-3-[(methylsulfonyl)oxy]heptyl acetate (12.615 g, 49 mmol). The reaction mixture was further stirred at room temperature for 20 hours and then poured into water and extracted several times with a heptane/toluene mixture (4/1). The organic layers were combined, washed with water and dried over anhydrous Na$_2$SO$_4$. After filtration and evaporation of the solvent under vacuum the crude product was purified by flash chromatography on silica gel eluted with a heptane/AcOEt (9/1) mixture to give pure (+)-(S)-3-(acetylthio)heptyl acetate (5.333 g, 47% over the two steps).

Optical rotation: $\alpha_D$=+8.7 (c=5.0, CHCl$_3$, 20° C.).

$^{1}$H-NMR: 4.13 (t, J=6.7, 2H), 3.65-3.58 (m, 1H), 2.32 (s, 3H), 2.05 (s, 3H), 2.03-1.94 (m, 1H), 1.89-1.79 (m, 1H), 1.7-1.5 (m, 2H), 1.45-1.25 (m, 4H), 0.89 (t, J=6.9, 3H).

$^{13}$C-NMR: 195.4 (s), 171.0 (s), 61.9 (t), 41.2 (d), 34.6 (t), 33.7 (t), 30.8 (q), 28.9 (t), 22.5 (t), 20.9 (q), 13.9 (q).

iv) (S)-3-Mercapto-1-heptanol

A 500 ml, four necked flask equipped with a mechanical stirring bar, a thermometer probe and an argon inlet/ outlet was charged with LiAlH$_4$ (2.15 g, 56.7 mmol) and Et$_2$O (180 ml). The mixture was cooled at c.a. 0° C. with an ice/water bath and a solution of (+)-(S)-3-(acetylthio)heptyl acetate (5.049 g, 22 mmol) in Et$_2$O (50 ml) was added over a period of 1 hour. More Et$_2$O (50 ml) was added to rinse. The cooling bath was removed and the reaction mixture was stirred at room temperature for 4 hours. Then, the reaction mixture was poured into ice, acidified with aqueous HCl 5N (100 ml), and extracted several times with Et$_2$O. The organic layers were combined and washed with water, aqueous saturated NaHCO$_3$, brine, and dried over anhydrous Na$_2$SO$_4$. After filtration and removal of the solvent under vacuum, the crude product was purified by flash chromatography on silica gel eluted with pentane/Et$_2$O (95/5) and then with Et$_2$O to give pure (S)-3-mercapto-1-heptanol (2.547 g, 79%).

Optical rotation: $\alpha_D$=+4.4 (c=5.0, CHCl$_3$, 20° C.).

$^1$H-NMR: 3.87-3.75 (m, 2H), 2.99-2.89 (m, 1H), 2.4 (brs, 1H), 2.01-1.92 (m, 1H), 1.72-1.6 (m, 2H), 1.57-1.44 (m, 2H), 1.43-1.25 (m, 2H), 1.41 (d, J=7.2, 1H), 0.91 (t, J=7.2, 3H).

$^{13}$C-NMR: 60.6 (t), 41.3 (t), 39.2 (t), 37.9 (d), 29.2 (t), 22.4 (t), 14.0 (q).

v) (S)-3-Mercaptoheptyl acetate

To a solution of (S)-3-mercapto-1-heptanol (2.364 g, 16 mmol) in CH$_2$Cl$_2$ (10 ml) was added dropwise at room temperature a solution of acetyl chloride (1.2 ml, 13.9 mmol) in CH$_2$Cl$_2$ (6 ml) over a period of 20 minutes. After 4 hours of stirring at room temperature, the reaction mixture was poured into brine and extracted several times with Et$_2$O. The organic phases were combined, washed with brine and dried over anhydrous Na$_2$SO$_4$. After filtration and removal of the solvent under vacuum, the crude product was purified by flash chromatography on silica gel eluted with pentane/Et$_2$O (95/5), followed by Kugelrohr distillation under vacuum to give pure (S)-(3-mercaptoheptyl acetate (S-10) (2.195 g, 11 mmol, 72%) as an orange liquid.

Optical rotation: $\alpha_D$=+7.3 (c=5.0, CHCl$_3$, 20° C.).

$^1$H-NMR: 4.29-4.19 (m, 2H), 2.91-2.81 (m, 1H), 2.05 (s, 3H), 2.07-1.98 (m, 1H), 1.78-1.62 (m, 2H), 1.56-1.45 (m, 2H), 1.42-.1.28 (m, 3H), 1.39 (d, J=7.2, 1H), 0.91 (t, J=7.4, 3H).

$^{13}$C-NMR: 170.95 (s), 62.3 (t), 38.8 (t), 37.76 (t), 37.6 (d), 29.1 (t), 22.4 (t), 20.9 (q), 14.0 (q).

B) Preparation of (R)-3-Mercaptoheptyl Acetate i) (S)-1,3-Heptanediol

To a suspension of LiAlH$_4$ (7.52 g, 198.2 mmol) in THF (100 ml) at 0° C. was added slowly a solution of (S)-methyl 3-hydroxyheptanoate (15.06 g, 94 mmol) in THF (25 ml) over a period of one hour. At the end of the addition, more THF (10 ml) was added to rinse and the reaction mixture was stirred at room temperature for 5 hours and 30 minutes. More LiAlH$_4$ (3.76 g, 99 mmol) was then added, and the reaction mixture was stirred for another 17 hours. Next, the reaction mixture was cooled with an ice-water bath and the reaction was stopped by adding successively H$_2$O (11.5 ml), aqueous NaOH 30% (11.5 ml) and H$_2$O (34 ml). The resulting white slurry was dried by adding anhydrous Na$_2$SO$_4$ (46 g) and filtered over a plug of celite thoroughly washed with THF. The solvent was removed under vacuum and the crude diol was purified by flash chromatography on silica gel eluted with a mixture of heptane/AcOEt (2/1) to give the desired compound (9.910 g, 80%) as a pale yellow oil.

$^1$H-NMR: 3.9-3.75 (m, 3H), 3.38 (br s, 1H), 3.23 (br s, 1H), 1.76-1.59 (m, 2H), 1.56-1.23 (m, 6H), 0.91 (t, J=7, 3H).

$^{13}$C-NMR: 72.0 (d), 61.5 (t), 38.3 (t), 37.5 (t), 27.8 (t), 22.7 (t), 14.1 (q).

(R)-3-Mercaptoheptyl acetate was then obtained by following the same experimental procedure as described above under A). The spectroscopic properties of the enantiomer (R) were the same as for the enantiomer (S) at the exception of the optical rotation:

$\alpha_D$=−7.5 (c=5.0, CHCl$_3$, 20° C.).

Example 3

Flavoring Composition and Flavored Articles Comprising 3-Mercaptoheptyl Acetate

A flavor composition having a "grapefruit character" was prepared by admixing the following ingredients:

| Ingredient | Parts by weight |
| --- | --- |
| Nootkatone | 0.1 |
| Linalool | 2.0 |
| Ethyl butyrate | 0.5 |
| Terpineol | 3.0 |
| Acetaldehyde | 1.0 |
| Octanal | 0.3 |
| Decanal | 0.1 |
| Citronellal | 2.0 |
| Geranyl Acetate | 0.5 |
| 1%* *Bucchu* oil | 0.5 |
| Ethanol | 990.0 |
| | 1000.0 |

*in ethanol

The addition of 1 part by weight of 3-Mercaptoheptyl acetate to the above described flavor composition provided a fruity-citrusy top note and imparted a long-lastingness of the citrus notes, giving a strong impression of juiciness, with slight bitterness reminding a tea aftertaste. The new composition thus obtained was named A).

When, instead of the invention's compound there was added the same amount of 1-methoxy-3-heptanethiol, the composition acquired an enhanced sulfury top-note and no effect on the after taste and the juiciness was perceivable. The new composition thus obtained was named B).

When, instead of the invention's compound there was added the same amount of 3-mercaptohexyl acetate the overall taste was changed in the direction of an overripe guava tonality, and no long-lastingness of the flavor was perceivable. The new composition thus obtained was named C).

When the compositions A), B), or C) were added into a carbonated soft drink at the level of 0.1% w/w in the finished drink. The organoleptic effects were similar to the ones described above. However, composition A) was also able to confer to the flavor of the finished drink a much impressive "body"/"fullness" comparable to that of grapefruit juice.

Example 4

Flavoring Composition and Flavored Articles Comprising 3-Mercaptoheptyl Acetate

A flavor composition having a "peach character" was prepared by admixing the following ingredients:

| Ingredient | Parts by weight |
| --- | --- |
| Octyl Acetate | 5.00 |
| Linalool | 1.50 |
| Gamma undecalactone | 0.50 |
| Delta decalactone | 1.00 |
| Isobutyric acid | 3.00 |
| Isopropyl methyl thiazol | 0.05 |
| 1%* *Ofmanthus* essential oil | 1.00 |
| Ethanol | 987.95 |
| | 1000.00 |

*in ethanol

The addition of 1 parts by weight of 3-mercaptoheptyl acetate to the above-described flavor composition provided a peach skin top note and imparted a long-lastingness related to the peach character as well as a juicy-fleshy character. The new composition thus obtained was named A).

When, instead of the invention's compound there was added the same amount of 1-methoxy-3-heptanethiol, the composition flavor profile became unbalanced and lacked of a long-lasting effect. The new composition thus obtained was named B).

When, instead of the invention's compound there was added the same amount of 3-mercaptohexyl acetate the overall taste became clearly of the type overripe guava and loosed the peach taste. The new composition thus obtained was named C).

When the compositions A), B), or C) were added into a tea drink at the level of 0.05% w/w in the finished drink. The organoleptic effects were similar to the ones described above. However, composition A) was also able to enhance the tea character of the finished drink.

What is claimed is:

1. A method to confer, enhance, improve or modify the flavor properties of a flavoring composition or flavored article, which method comprises adding to the composition or article the compound 3-mercaptoheptyl acetate or an optically active enantiomer thereof in an amount effective to provide a flavor base having top notes of a citrus, tea and/or peach and/or berries and/or tropical fruit without flavors of onion, grilled meat, rhubarb or carrot.

2. The method according to claim 1, wherein the compound is added to provide an amount of from 0.0001 to 500 ppm in the flavoring composition or flavored article.

3. The method according to claim 1, wherein the compound is added to provide an amount of from 0.0003 to 5 ppm in flavored article.

4. The method according to claim 1, wherein the compound is present in a flavoring composition that is added to the flavored article.

5. The method according to claim 4, wherein the flavoring composition comprises at least one ingredient selected from the group consisting of a flavor carrier and a flavor base; and optionally at least one flavor adjuvant.

6. The method according to claim 4, wherein the compound is provided in the flavoring composition in an amount of from 0.0000001 to 0.03% by weight thereof.

7. The method according to claim 4, wherein the compound is provided in the flavoring composition in an amount of from 0.0000002 to 0.01% by weight thereof.

8. The method according to claim 1, wherein the flavored article includes a foodstuff base which is a bakery, a dairy, a confectionary, a savory, an infusion, a soft drink, a flavored water or a juice product.

9. A flavoring composition comprising:
   i) as flavoring ingredient, the compound 3-mercaptoheptyl acetate or an optically active enantiomer thereof in an amount effective to provide a flavor base having top notes of a citrus, tea and/or peach and/or berries and/or tropical fruit without flavors of onion, grilled meat, rhubarb or carrot;
   ii) at least one ingredient selected from the group consisting of a flavor carrier and a flavor base; and
   iii) optionally at least one flavor adjuvant.

10. A flavored article comprising:
    as flavoring ingredient, the compound 3-mercaptoheptyl acetate or an optically active enantiomer thereof in an amount effective to provide a flavor base having top notes of a citrus, tea and/or peach and/or berries and/or tropical fruit without flavors of onion, grilled meat, rhubarb or carrot; and
    a foodstuff base.

11. The flavored article according to claim 10, wherein the compound is added to provide an amount of from 0.0001 to 120 ppm in the flavored article.

12. The flavored article according to claim 10, wherein the compound is provided in an amount of from 0.0003 to 5 ppm in the flavored article.

13. The flavored article according to claim 12, wherein the compound is present in a flavoring composition that is present in the flavored article.

14. The flavored article according to claim 13, wherein the flavoring composition comprises at least one ingredient selected from the group consisting of a flavor carrier and a flavor base; and optionally at least one flavor adjuvant.

15. The flavored article according to claim 14, wherein the compound is provided in the flavoring composition in an amount of from 0.0000001 to 0.03% by weight thereof.

16. The flavored article according to claim 14, wherein the compound is provided in a flavoring composition in an amount of from 0.0000002 to 0.01% by weight thereof.

17. The flavored article according to claim 10, wherein the foodstuff base is a bakery, a dairy, a confectionary, a savory, an infusion, a soft drink, a flavored water or a juice product.

18. The method according to claim 1, wherein the citrus is grapefruit.

19. The flavoring composition of claim 9, wherein the citrus is grapefruit.

20. The flavored article of claim 10, wherein the citrus is grapefruit.

* * * * *